United States Patent [19]
Kume et al.

[11] Patent Number: 5,411,016
[45] Date of Patent: May 2, 1995

[54] INTRAVASCULAR BALLOON CATHETER FOR USE IN COMBINATION WITH AN ANGIOSCOPE

[75] Inventors: Stewart M. Kume, Plymouth; Trac Le, Columbia Heights; Roger N. Hastings, Maple Grove, all of Minn.

[73] Assignee: Scimed Life Systems, Inc., Maple Grove, Minn.

[21] Appl. No.: 200,122

[22] Filed: Feb. 22, 1994

[51] Int. Cl.⁶ ............... A61B 1/06; A01M 25/00; A01M 29/00
[52] U.S. Cl. ............... 128/6; 604/96; 606/192
[58] Field of Search ............... 604/96–103, 604/280, 271; 606/192–195; 128/4–11

[56] References Cited

U.S. PATENT DOCUMENTS

| | | |
|---|---|---|
| Re. 34,544 | 2/1994 | Spears . |
| 4,040,413 | 8/1977 | Ohshiro . |
| 4,224,929 | 9/1980 | Furihata . |
| 4,331,132 | 5/1982 | Mukasa . |
| 4,445,892 | 5/1984 | Hussein et al. . |
| 4,470,407 | 9/1984 | Hussein . |
| 4,619,247 | 10/1986 | Inoue et al. . |
| 4,676,231 | 6/1987 | Hisazumi . |
| 4,773,899 | 9/1988 | Spears . |
| 4,779,611 | 10/1988 | Grooters et al. . |
| 4,784,133 | 11/1988 | Mackin . |
| 4,799,479 | 1/1989 | Spears . |
| 4,808,164 | 2/1989 | Hess . |
| 4,878,725 | 11/1989 | Hessel et al. . |
| 4,886,496 | 12/1989 | Conoscenti et al. . |
| 4,892,099 | 1/1990 | Ohkawa et al. . |
| 4,921,484 | 5/1990 | Hillstead . |
| 4,927,413 | 5/1990 | Hess . |
| 4,961,738 | 10/1990 | Mackin . |
| 4,976,710 | 12/1990 | Mackin . |
| 5,007,898 | 4/1991 | Rosenbluth et al. . |
| 5,019,075 | 5/1991 | Spears et al. . |
| 5,029,574 | 7/1991 | Shimamura . |

(List continued on next page.)

FOREIGN PATENT DOCUMENTS

WO90/00914 2/1990 WIPO .

OTHER PUBLICATIONS

"VII. Angioscopy and Ultrasound Guidance," *Lasers in Cardiovascular Medicine and Surgery:Fundamentals and Techniques*, Yasumi Uchida, pp. 399–422, 1990.
"More Brightness for Excellence in Intraluminal Diagnostics!" 8-p. brochure from Ad Krauth, undated.

*Primary Examiner*—John D. Yasko
*Assistant Examiner*—Adam J. Cermak
*Attorney, Agent, or Firm*—Robert E. Atkinson

[57] ABSTRACT

A balloon dilatation catheter is disclosed which incorporates an elongate shaft which is at least partially optically transparent. The shaft includes an inflation lumen and a guide wire lumen extending therethrough in addition to an inflatable balloon connected to its distal end. The inflatable balloon may include a measuring index disposed thereon. The measuring index may comprise a plurality of longitudinally-spaced radial bands, a plurality of radially-spaced longitudinal bands, or a combination thereof. A method of using an angioscope in combination with a balloon catheter is also disclosed. The method involves inserting a balloon catheter with an optically transparent shaft section into a vascular lumen, inserting an angioscope into the balloon catheter, inflating the balloon on the balloon catheter, and measuring material characteristics of abnormal deposits therein. The material characteristics may be measured by the color of the abnormal deposit or the response of the abnormal deposit to inflation of the balloon.

8 Claims, 6 Drawing Sheets

U.S. PATENT DOCUMENTS

| | | |
|---|---|---|
| 5,030,227 | 7/1991 | Rosenbluth et al. . |
| 5,036,463 | 6/1991 | Abela et al. . |
| 5,071,429 | 12/1991 | Pinchuk et al. . |
| 5,078,681 | 1/1992 | Kawashima . |
| 5,090,959 | 2/1992 | Samson et al. . |
| 5,092,841 | 3/1992 | Spears . |
| 5,103,804 | 4/1992 | Abele et al. . |
| 5,116,317 | 5/1992 | Carson et al. . |
| 5,117,831 | 6/1992 | Jang et al. . |
| 5,125,925 | 6/1992 | Lundahl . |
| 5,152,277 | 10/1992 | Honda et al. . |
| 5,159,920 | 11/1992 | Condon et al. . |
| 5,163,950 | 11/1992 | Pinchuk et al. . |
| 5,167,233 | 12/1992 | Eberle et al. . |
| 5,169,395 | 12/1992 | Narcisco, Jr. ............................ 606/7 |
| 5,188,596 | 2/1993 | Condon et al. . |
| 5,199,951 | 4/1993 | Spears . |
| 5,201,317 | 4/1993 | Kanazawa et al. . |
| 5,203,337 | 4/1993 | Feldman . |
| 5,263,928 | 11/1993 | Trauthen et al. . |
| 5,292,305 | 3/1994 | Boudewijn et al. . |
| 5,293,872 | 3/1994 | Alfano et al. . |
| 5,330,467 | 7/1994 | Abela ..................................... 606/15 |

INTRAVASCULAR BALLOON CATHETER FOR USE IN COMBINATION WITH AN ANGIOSCOPE

FIELD OF THE INVENTION

The present invention generally relates to intravascular devices and methods of use thereof. More specifically, the present invention relates to balloon angioplasty devices for use in combination with an angioscope.

BACKGROUND OF THE INVENTION

A wide variety of devices and techniques have been developed to diagnose and treat vascular diseases. Coronary artery disease (CAD) is a vascular disease in which blood flow to the heart muscle is restricted by abnormal deposits in the coronary arteries. The abnormal deposits deprive portions of the heart muscle of essential oxygenated blood. The wide spread impact of coronary artery disease has stimulated the development of diverse types of therapeutic and diagnostic devices.

Percutaneous transluminal coronary angioplasty (PTCA) has gained wide acceptance as an effective and minimally invasive method of treating coronary artery disease. A typical PTCA procedure involves the use of an angioplasty balloon catheter. Examples of over-the-wire type balloon catheters are described in commonly assigned U.S. Pat. Nos. 4,976,690 to Solar, and 5,047,045 to Arney. The balloon catheter is inserted into the body by way of the femoral artery and is navigated to a coronary artery, assisted by a guide catheter and a guide wire. The balloon is positioned across a restriction in the artery and the balloon is subsequently inflated. The inflated balloon compresses the restriction outwardly, thus opening the restriction and restoring blood flow to portions of the heart muscle previously deprived of oxygenated blood.

Other minimally invasive techniques have been developed as alternatives to balloon PTCA. For example, atherectomy devices are designed to treat specific types of lesion morphology. Atherectomy, as distinguished from balloon PTCA, removes the abnormal deposit or lesion from the vessel rather than molding or compressing the restriction with a balloon.

Other medical devices have been developed for use in combination with balloon PTCA. Balloon expandable stents, for example, are used post-PTCA to prevent a dilated restriction from re-closing. A balloon-expandable stent is delivered to the location of the dilated restriction using a balloon catheter. The stent is mounted in its collapsed position onto a deflated balloon and the balloon catheter is navigated through the vasculature to the portion of the vessel previously dilated. The balloon is expanded to open the stent causing it to engage the inner wall of the vessel. The balloon is then deflated and the balloon catheter is removed, leaving the stent securely in place across the dilated restriction.

PTCA balloon catheters, atherectomy devices, stents as well as several other intravascular devices require some means to visualize the operation of the devices while inside the body. The most common method of visualization is angiography. Angiography involves the injection of radiopaque contrast fluid into the vessel while simultaneously viewing the subject vessel radiographically. Angiography is limited to viewing the subject vessel in a monochromatic two-dimensional plane with no depth of field. To partially compensate for this limitation, a plurality of planar views can be taken and a three dimensional view can be mentally assimilated. However, this method inherently involves a certain amount of human error and since each view must be taken in sequence, critical time is wasted which may jeopardize the health of the patient. In addition, since angiography is limited to monochromatic views, it is not able to accurately identify the pathology of abnormal deposits within the vessel.

Angioscopes, by contrast, allow the treating physician to view a vessel in a multi-chromatic two dimensional plane with depth of field. The ability to view in two dimensions with depth of field allows the physician to ascertain the morphology of the vessel and the obstructive material in a more accurate and timely manner. Furthermore, the ability to view in color allows the physician to identify the pathology of the obstructive material (e.g. thrombus, plaque and the like). By utilizing angioscopy, the physician can modify the therapy as a function of the pathology and morphology of the obstructive material in the vessel.

Intravascular angioscopy requires a means to displace optically opaque blood from the field of view. The most common method of displacing opaque fluid utilizes an occluding balloon to block the flow of blood proximal to the portion of the vessel to be viewed. An optically transparent fluid such as saline is then flushed distal of the occluding balloon and the angioscope can then view through the optically transparent fluid. However, utilizing an occluding balloon deprives portions of the heart of essential oxygenated blood and often results in ischemia and patient discomfort. As such, this method is limited to short intervals typically 30 to 45 seconds. Also, the profile of such occluding balloon catheters is large because the catheter must provide a large flush lumen in addition to an inflation lumen, a guide wire lumen and an angioscope lumen. It is desirable to minimize the profile for intravascular applications. In addition, some of the prior art devices that utilize this method include integral angioscopes which are not removable and thus inherently increases the cost of the device.

Another method of displacing optically opaque fluid from the field of view utilizes a fluid displacing balloon. In this method, a balloon is inflated with an optically transparent fluid such as saline and is thereby expanded to come into contact with the interior of the vessel. The angioscope can then view through the optically transparent fluid. However, the prior art devices that utilize this method include integral angioscopes which are not removable and thus inherently increase the cost of the device. Also, the profile of such occluding balloon catheters is large because the catheter must provide an angioscope lumen in addition to an inflation lumen and a guide wire lumen. Again, it is desirable to minimize the profile of intravascular devices in order to have access to small diameter vessels.

In addition, prior art intravascular angioscopes do not provide a means to collect quantitative information about the vessel and obstructions within the vessel. Angiography, by contrast, provides some quantitative information but is limited to measuring dimensions in only one plane. As such, it is desirable to retain all the benefits of angioscopy and provide a means to gain quantitative information.

Examples of intravascular angioscopes include the device disclosed in U.S. Pat. No. 4,470,407 to Hussein. Hussein '407 discloses an endoscopic device including an elongated tube carrying an expandable balloon on its distal end which displaces opaque fluid such as blood and allows for viewing of the walls of the duct which come into contact with the balloon. In addition, U.S. Pat. No. 5,090,959 to Samson et al. discloses an imaging balloon dilation catheter for use in angioplasty. Further, U.S. Pat. No. 5,116,317 to Carson Jr., et al. discloses a balloon-type catheter with an integral optical system for use in angioplasty.

In general, it is desirable to have an over-the-wire type dilating balloon catheter for use in combination with an angioscope. In particular, it is desirable to be able to manipulate and navigate such a balloon catheter independent of the angioscope. It is also desirable to be able to exchange a first balloon catheter for a second balloon catheter without wasting the integral angioscope of the first balloon catheter. Additionally, it is desirable to have quick and easy access to the treatment site with the angioscope when the catheter is already in place. It is further desirable to visualize different areas of the treatment site while the therapy is in progress and to have the ability to quantitatively assess dimensional aspects of the objects being viewed.

Thus, there is a need for a device which satisfies these desirable aspects and overcomes the associated disadvantages of the prior art. The present invention overcomes the disadvantages of the prior art and additionally provides several novel features that can be appreciated in review of the following summary and detailed description of the invention.

SUMMARY OF THE INVENTION

The present invention can be described as an over-the-wire type vascular balloon catheter including a long shaft where the distal portion of the shaft within the balloon is optically transparent. The optically transparent shaft section allows an angioscope to visualize the treatment site of the vessel while balloon dilation is in progress.

The optically transparent shaft section of the present invention may define the guide wire lumen such that the angioscope is insertable therein. The ability to use an angioscope within the guide wire lumen provides quick and simple access for the angioscope to the therapy site when the balloon catheter is already in position. The ability to slide the angioscope within the balloon catheter allows for visualization at various longitudinal positions along the length of the vessel and particularly at the treatment site. As distinguished from a balloon catheter with an integral angioscope, the ability to remove the angioscope allows a first balloon catheter to be exchanged for a second balloon catheter without wasting the angioscope of the first balloon catheter.

The present invention can also be described as a vascular balloon catheter including a measuring index covering at least a portion of the inflatable balloon to allow for optical measurement of a surface of a vessel. This allows the physician to quantitatively assess dimensional aspects of the objects being viewed. In particular, it provides a means for quantitative optical measurement of portions of the lumen that come into contact with the balloon.

The present invention can also be described in terms of its unique methods of use. For example the present invention is able to monitor balloon inflation without the use of angiography. It is beneficial to minimize the need for angiography because radiation can be harmful in significant doses.

The present invention can further be used to visualize the vessel lumen upon inflation of the balloon to assist in quantifying the length and diameter of the restriction before, during and after pressurized balloon dilation.

Additionally, the balloon catheter of the present invention can be inflated to a low pressure so as to conform the balloon to the geometry of the restriction within the vessel. The angioscope can then be used to view the interior of the balloon which conforms to the restriction of the vessel and thereby quantitatively analyze the morphology or topography of the restriction. Alternatively, by inflating the balloon slowly and monitoring the diameter of the balloon as a function of pressure, the physical characteristics of the lesion material can be calculated to determine its pathology or composition.

The balloon catheter of the present invention can also be used to deliver a stent such that the angioscope is used to monitor stent expansion through the balloon and confirm complete and accurate deployment of the stent.

BRIEF DESCRIPTION OF THE DRAWINGS

The following drawings are referenced in the text of the detailed description of the invention. Several figures are presented in which like numerals in different figures refer to identical parts.

DETAILED DESCRIPTION OF THE INVENTION

Figure 1:
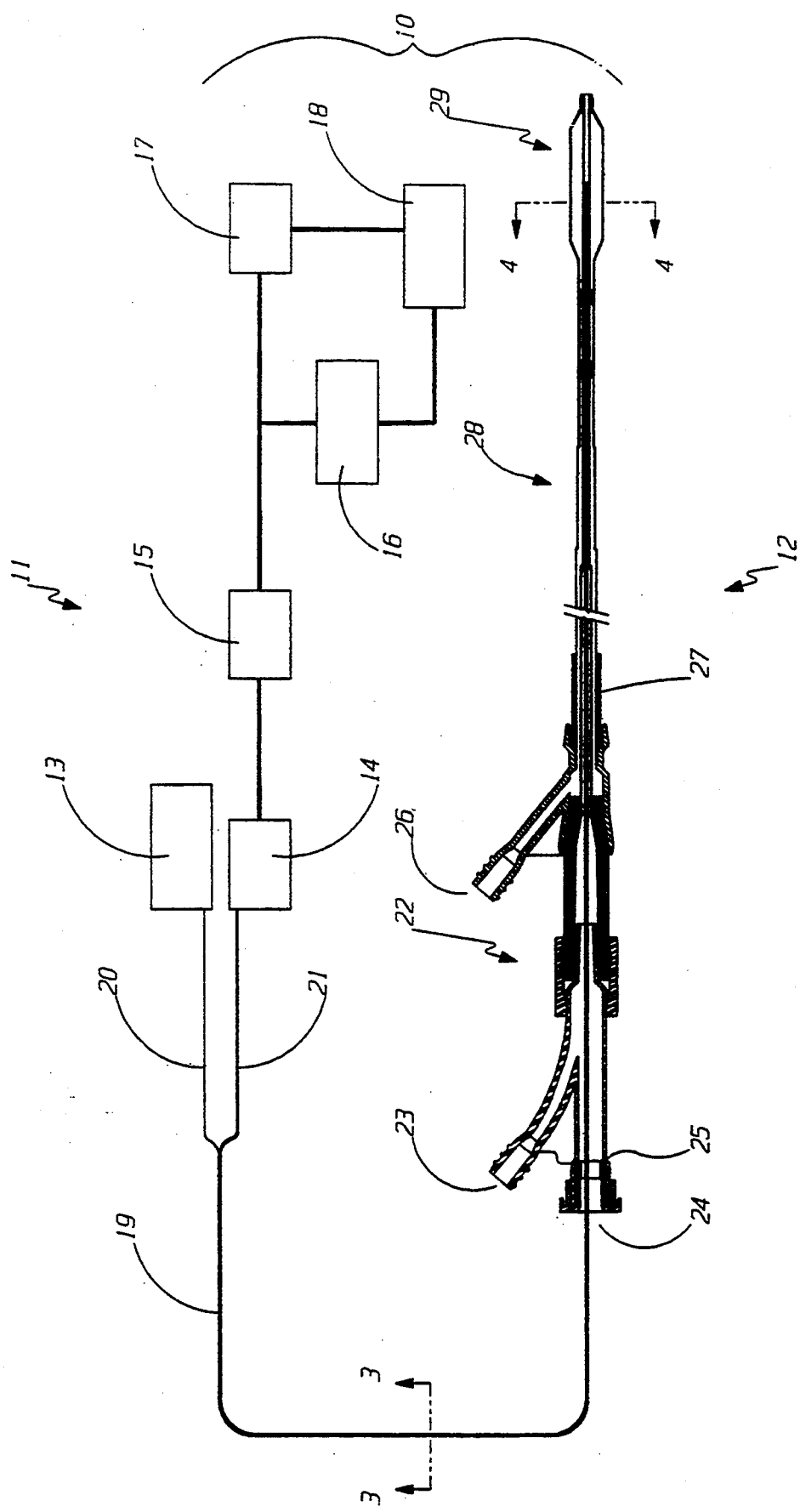
FIG. 1 is a plan view of a preferred embodiment of the present invention with portions in sectional view.

Referring to FIG. 1, a medical system 10 in accordance with the present invention includes an angioscopy system 11 and a balloon catheter 12. The angioscopy system 11 includes an angioscope 19 which is includes a plurality of illumination fibers 20 and an imaging bundle 21 with an objective lens at its distal end (not shown). The proximal end of the illumination fibers 20 are connected to a light source 13. The proximal end of the imaging bundle 21 is connected to a series of image processing subsystems, including focusing optics 14, camera 15, computer 16, video cassette recorder (VCR) 17, and video monitor 18. The light source and the image processing subsystems can be arranged as well known in the art such as shown in U.S. Pat. No. 4,331,132 to Mukasa, which is herein incorporated by reference. The computer 16 can be used to digitally enhance the image and/or quantitatively process the image in order to determine dimensional aspects of the objects being viewed. The dimensional aspects can be calculated by knowing the total magnification of the focusing optics 14 and the distance from end of the angioscope to the measuring index 46, 47 on the balloon.

Balloon catheter 12 includes a manifold assembly 22 at its proximal end, a catheter shaft 28 and an inflatable balloon 29 at its distal end. The manifold assembly 12 is preferably made of injection molded polycarbonate, however, those skilled in the art will recognize that alternate materials can be used.

The manifold assembly 22 includes a flush port 23 which is adapted to be connected to a pressurized fluid supply such as a syringe filled with saline. The flush port 23 is in fluid communication with a guide wire lumen 43, best shown in FIG. 2, which extends through the catheter shaft 28. Saline can be flushed into flush port 23 prior to using the device so as to remove all air trapped in the guide wire lumen 43. Fluid can also be flushed through flush port 23 during use of the device to clear away blood and unwanted debris. The flush port 23 can also be used to inject contrast media adjacent to and distal from the treatment site.

The manifold assembly 22 also includes an imaging tube port 24 in combination with a hemostatic seal 25 which are sized to allow the insertion and removal of angioscope 19 or a guide wire (not shown). In one preferred embodiment of the balloon catheter 12, the guide wire lumen 43 would be dimensioned to accept an 0.018 diameter guide wire. As such, the guide wire (not shown) would need to be removed to advance the angioscope 19 to the therapy site. However, the guide wire lumen 43 could also be dimensioned to accept both a guide wire and an imaging tube simultaneously.

In use, the hemostatic seal 25 is used to seal around either the angioscope 19 or the guide wire (not shown) so as to prevent blood from entering the distal end of the catheter and exiting out the guide wire port 24. The hemostatic seal 25 also allows for fluid to be flushed into the guide wire lumen 43 about the angioscope 19 to clear away blood and unwanted debris.

Figure 2:
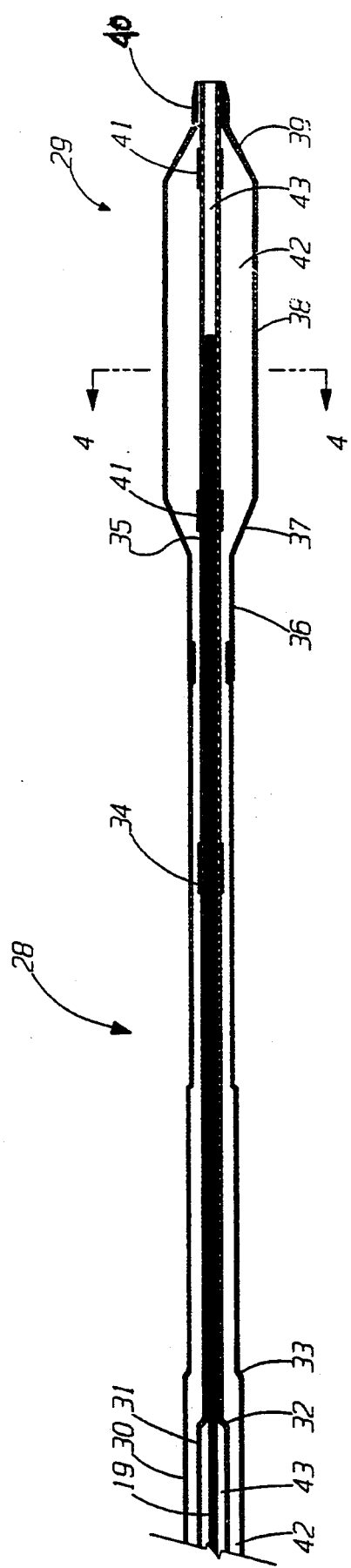
FIG. 2 is a sectional drawing of a preferred embodiment of the distal portion of the catheter of the present invention.

The manifold assembly 22 also includes a balloon inflation port 26 which is in fluid communication with an inflation lumen 42, best shown in FIG. 2. The balloon inflation port 26 is adapted to be connected to a pressurized fluid source such as an inflation device that allows for a selective inflation and deflation of the inflation balloon 29.

The proximal end of the catheter shaft 28 is connected to the manifold assembly 22. A strain relief 27 is preferably incorporated to prevent kinking between the relatively stiff manifold assembly 22 and the relatively flexible catheter shaft 28. The strain relief 27 is preferably made of extruded polyolefin and is dimensioned to fit over the catheter shaft 28 and into manifold assembly 22.

Referring now to FIG. 2, the catheter shaft 28 includes an outer tube 30 connected at its proximal end to the manifold assembly 22 and connected at its distal end to the proximal balloon waist 36 by means of a suitable adhesive such as epoxy or urethane. The outer tube 30 also includes a series of tapers 33 to facilitate varying flexibility along the length of the catheter shaft 28. The outer tube 30 is preferably made of extruded polyethylene with outer tapers 33 formed by drawing the outer tube 30 through a reduced diameter heated dye. The outer tube is preferably approximately 135 cm. long and tapers from approximately 0.0474–0.0522 inches at the proximal end to approximately 0.031–0.047 inches at the distal end. Those skilled in the art will recognize that the outer tube 30 can be formed of alternate materials and dimensions as are conventional in the art.

The catheter shaft 28 also includes an inner tube 31 which is connected at its proximal end to the manifold assembly 22 and at its distal end to an optically-transparent tube 35. Junction tube 34 serves to connect the inner tube 31 to the optically-transparent tube 35 by means of a suitable adhesive such as epoxy or urethane. Inner tube 31 also includes a series of tapers 32 which impart varying flexibility along the length of the catheter shaft 28. The inner tube 31 is manufactured in a similar manner as outer tube 30. Inner tube 31 is preferably made of extruded polyethylene and is approximately 137 cm. long. The inner tube tapers from 0.027–0.029 inches at the proximal end to approximately 0.023–0.025 inches at the distal end. The inner tube 31 can also be formed of various other materials and dimensions which are conventional in the art. Junction tube 34 is preferably made of a thin-walled polymer tube such as polyimide so as to minimize interference with the inflation lumen 42.

Alternatively, rather than incorporate junction tube 34, the optically transparent tube 35 may incorporate a proximal flared portion (not shown) to connect to the distal end of the inner tube 31 by means of a suitable adhesive. The need for junction tube 34 can also be eliminated by forming the optically transparent tube 35 as an integral continuation of inner tube 31 such that the entire inner tube 31 is formed of an optically transparent material.

The optically-transparent tube 35 is connected at its distal end to the distal balloon waist 40 by means of a suitable adhesive such as epoxy or urethane. The optically-transparent tube is preferably formed of polycarbonate but can be formed of any optically-transparent material with a preferable optical index of refraction between approximately 1.3 and 1.6. Those skilled in the art will recognize that any optically-transparent polymer may be used. However, it is preferable to match the index of refraction of the optically-transparent tube 35 to the fluid used to inflate the balloon.

Radiopaque marker bands 41 are secured to the optically-transparent tube 35 to facilitate radiographic placement of the balloon catheter at the therapy site. The marker bands 41 are preferably aligned with the proximal balloon cone 37 and distal balloon cone 39 so as to not interfere with angioscopic visualization. The marker bands 41 can be made of any suitable material conventional in the art such as gold, platinum or an alloy thereof.

Figure 3:
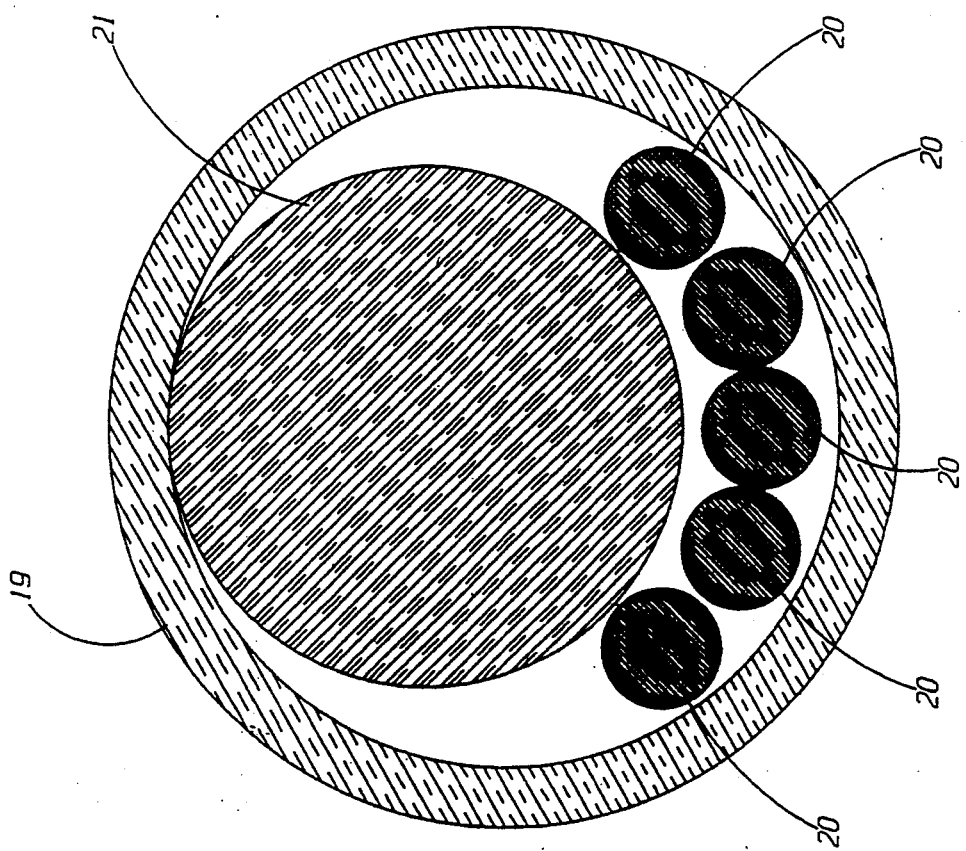
FIG. 3 is a cross-sectional view of FIG. 1 taken at 3—3.
Figure 4:
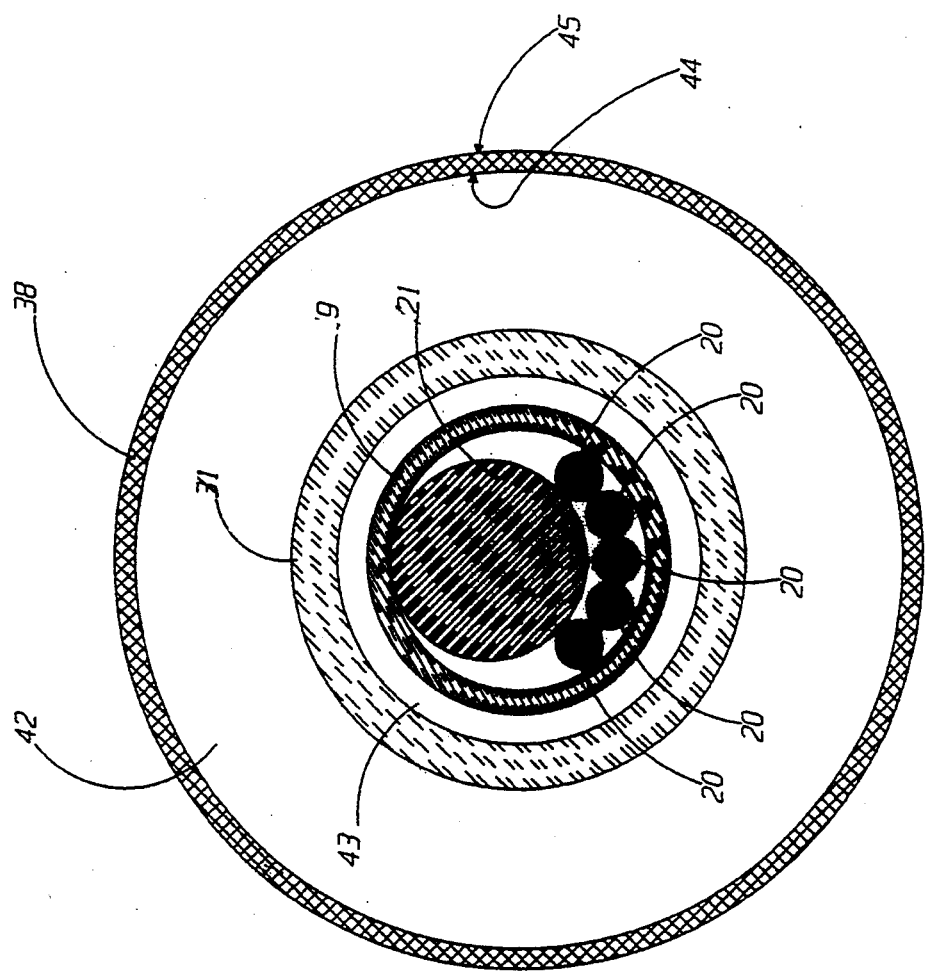
FIG. 4 is a cross-sectional view of FIG. 1 taken at 4—4.

Referring now to FIGS. 3 and 4, angioscope 19 is disposed in the guide wire lumen 43 and includes an imaging bundle 21 and a plurality of illumination fibers 20. The imaging bundle 21 and illumination fibers 20 are substantially as described in U.S. Pat. No. 5,116,317 to Carson, Jr. et al. which is herein incorporated by reference. Those skilled in the art will recognize that other angioscopes be used with the present invention.

Figure 5:
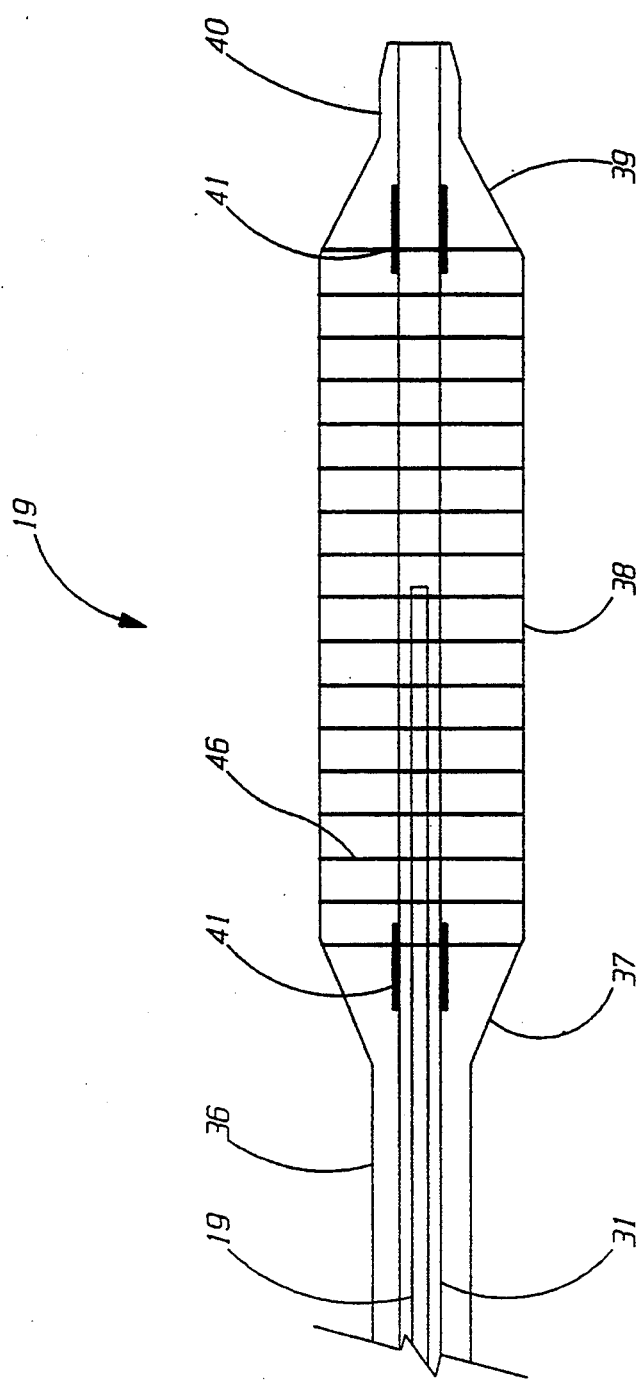
FIG. 5 is a side view of a preferred embodiment of a measuring index for use with the present invention.

To facilitate quantitative analysis of the objects being viewed by the angioscope through the balloon catheter 12, a measuring index may be incorporated on the inflatable balloon 29. The measuring index can then be compared relative to an object or a topography being viewed and precise dimensions can be calculated therefrom. For example, in a first preferred embodiment of the measuring index for use with the present invention as shown in FIG. 5, the inflatable balloon 29 may include a series of radial bands 46 spaced apart in equal increments of a known dimension. Either by visualizing the radial bands 46 on the video monitor 18 or by utilizing the computer 16, the diameter of the balloon 29 can be determined at each radial band position. The radial bands 46 can be formed on the outer surface 45 of the transparent balloon 29 using a permanent ink marker. The ink should be substantially opaque such that they can be clearly seen with the angioscope. Alternatively, the radial bands 46 can be made of fluorescent ink to enhance visualization. Furthermore, the radial bands 46 can be formed of phosphorescent ink which may negate the need for a light source 13 and illumination fibers 20. The radial bands 46 preferably span the body of the balloon 38 between the proximal balloon cone 37 and the distal balloon cone 39.

Figure 6:
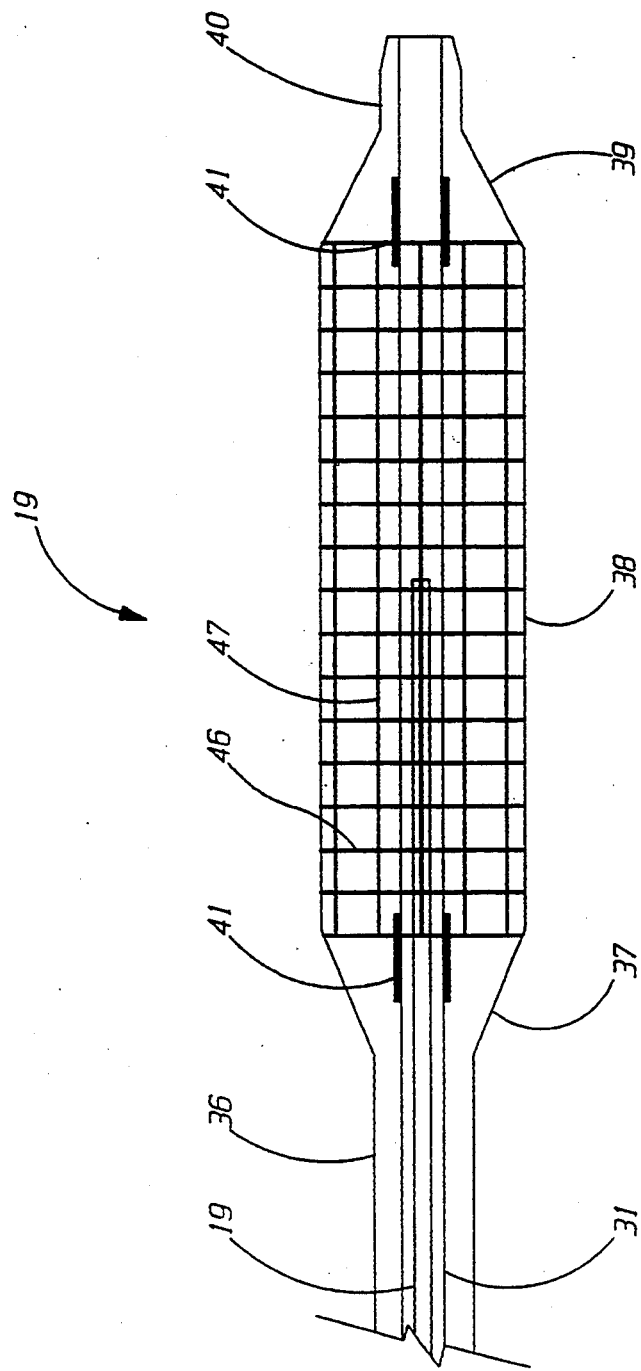
FIG. 6 is a side view of a second preferred embodiment of a measuring index for use with the present invention.

As shown in FIG. 6, a second preferred embodiment of a measuring index for use with the present invention includes the inflatable balloon 29 with both radial bands 46 and longitudinal bands 47. Both the radial bands 46 and longitudinal bands 47 are spaced equally apart at some known distance. In addition to the diameter calculated from the radial bands 46, the longitudinal bands 47 can be used to calculate the topography of the inflatable balloon 29 which conforms to the vessel when inflated. The longitudinal bands 47 are formed in substantially the same way as radial bands 46.

Referring back to FIGS. 4, 5 and 6, the inflatable balloon 29 includes inner surface 44 and outer surface 45. The radial bands 46 and the longitudinal bands 47 may be formed on either surface or between the surfaces by means of a laminate. If the bands 46 and 47 are formed on the outer surface, it is necessary that the balloon 29 be formed of an optically transparent material such as a polyolefin copolymer so that the bands are visible. In addition, if objects outside the balloon 29 are to be viewed, it is necessary that the balloon material be optically transparent so that those objects are visible. A balloon material which is not optical transparent is useful to visualize the inside surface of the balloon 44 which will conform to the topography of the vessel upon inflation of the balloon 29.

Referring back to FIG. 1, the device may be used as follows. First, a guide wire (not shown) is navigated through the vasculature to the target site. The balloon catheter 12 is placed over the guide wire and advanced such that the balloon 29 is placed across the target site. The guide wire is then removed and the angioscope is advanced into guide wire port 24 and through the guide wire lumen 43 until the distal end of the angioscope 19 is located within the balloon 29. The balloon 29 can then be inflated to dilate a restriction in the vessel and the progress of the balloon inflation can be monitored by way of the angioscope. The balloon also serves to displace all opaque fluid (blood) so that a clear image of objects outside the balloon 29 can be obtained through the optically-transparent tube 35, the inflation media (not shown) and the balloon 29.

Alternatively, the medical system 10 can be used to deliver an expandable stent, while monitoring the progress of deployment and expansion of the stent by use of the angioscope viewing from within the balloon. In the event that the angioscope indicates that the stent is not properly deployed, steps can be subsequently taken to correct the defective deployment. Corrective measures include re-inflating the balloon against the stent, removing the stent and deploying an additional stent.

The medical system 10 can also be used to determine the geometry and characteristic of a restriction in a vessel. To perform these functions, the balloon can be inflated to a low pressure so as to conform the balloon to the geometry of the restriction within the vessel. The angioscope can then be used to view the interior of the balloon which conforms to the restriction of the vessel and quantitatively analyze the topography of the restriction. The angioscope can also be used to monitor the topography of the restriction as a function of pressure. This in turn correlates to physical characteristics of the restriction.

The vessel lumen may also be visualized upon inflation of the balloon to assist in quantifying the maximum inflated diameter of the balloon which corresponds to the maximum inflated diameter of the restriction.

Other advantages of the present invention can be appreciated with a thorough review of the specification. Workers skilled in the art will recognize that changes can be made to the embodiments described herein without departing from the spirit or scope of the present invention. Accordingly, the following claims define the scope of the present invention.

The following is claimed:

1. A vascular balloon catheter, comprising:
   an elongate shaft having a proximal portion, a distal portion, an inflation lumen extending therethrough, the distal portion of the shaft being optically transparent;
   an inflatable balloon secured to the distal end of the elongate shaft, the balloon being in fluid communication with the inflation lumen;
   a guide wire lumen extending through the elongate shaft;
   an angioscope extending through the guide wire lumen such that the angioscope can visualize through the optically transparent shaft portion to an interior of a vascular lumen; and
   a measuring index on the inflatable balloon.

2. A vascular balloon catheter, comprising:
   an elongate shaft having a proximal end, a distal end and an inflation lumen extending therethrough;
   an inflatable balloon secured to the distal end of the elongate shaft, the balloon being in fluid communication with the inflation lumen; and
   a measuring index covering at least a portion of the inflatable balloon to allow for optical measurement of an object inside a vessel.

3. The vascular balloon catheter of claim 2, further comprising:
   a guide wire lumen extending through the elongate shaft; and
   an angioscope extending through the guide wire lumen such that the angioscope can visualize the measuring index through the guide wire lumen.

4. The vascular balloon catheter of claim 2, wherein the measuring index comprises a plurality of longitudinally spaced radial bands.

5. The vascular balloon catheter of claim 2, wherein the measuring index comprises a plurality of radially spaced longitudinal bands.

6. A method of using an angioscope in combination with a balloon catheter, the steps comprising:
   inserting an angioplasty balloon catheter with an optically-transparent shaft section into a vascular lumen;
   inserting an angioscope into the balloon catheter;
   inflating the balloon of the balloon catheter;
   monitoring the balloon inflation with the angioscope:
   viewing the interior surface of an abnormal deposit within a vessel with the angioscope; and measuring the material characteristics of the abnormal deposit.

7. The method of claim 6, wherein the material characteristics of the abnormal deposit are measured by the color of the abnormal deposit.

8. The method of claim 6, wherein the material characteristics of the abnormal deposit are measured by the observed response of the material to the inflation of the balloon.

* * * * *

UNITED STATES PATENT AND TRADEMARK OFFICE
CERTIFICATE OF CORRECTION

PATENT NO. : 5,411,016

DATED : May 2, 1995

INVENTOR(S) : KUME et al.

It is certified that error appears in the above-identified patent and that said Letters Patent is hereby corrected as shown below:

At column 2, line 9, "Angloscopes" should be --Angioscopes--.

Signed and Sealed this

Second Day of March, 1999

Attest:

Q. TODD DICKINSON

Attesting Officer

Acting Commissioner of Patents and Trademarks